United States Patent [19]
Levy

[11] Patent Number: 5,213,499
[45] Date of Patent: May 25, 1993

[54] ENDODONTIC FILES

[75] Inventor: Philippe Levy, San Clemente, Calif.

[73] Assignee: Laser Endo Technic, San Clemente, Calif.

[21] Appl. No.: 826,777

[22] Filed: Jan. 28, 1992

[51] Int. Cl.⁵ .............................................. A61C 5/02
[52] U.S. Cl. ..................................................... 433/102
[58] Field of Search ................................. 433/102, 224

[56] References Cited

U.S. PATENT DOCUMENTS

| | | | |
|---|---|---|---|
| 498,554 | 5/1893 | Johanson | 433/102 |
| 1,307,446 | 6/1919 | Kerr | 433/102 |
| 1,969,808 | 8/1932 | Lentulo | 433/224 |
| 4,231,738 | 11/1980 | Riitano et al. | 433/102 |
| 4,260,379 | 4/1981 | Groves et al. | 433/102 |
| 4,332,561 | 6/1982 | McSpadden | 433/102 |

FOREIGN PATENT DOCUMENTS 837146 4/1952 Fed. Rep. of Germany ...... 433/102

OTHER PUBLICATIONS

Hygenic catalogue, the Hygenic Corporation, May 1984.

Primary Examiner—John J. Wilson
Assistant Examiner—Cindy A. Cherichetti
Attorney, Agent, or Firm—Spensley Horn Jubas & Lubitz

[57] ABSTRACT

An endodontic file comprising a handle and an elongate cutting portion, a distal end remote from the handle and formed to have a first file portion which is adjacent the distal end and has the physical form of a k file, and a second file portion, which is located between the first portion and the handle and has the physical form of a Hedstrom file.

11 Claims, 1 Drawing Sheet

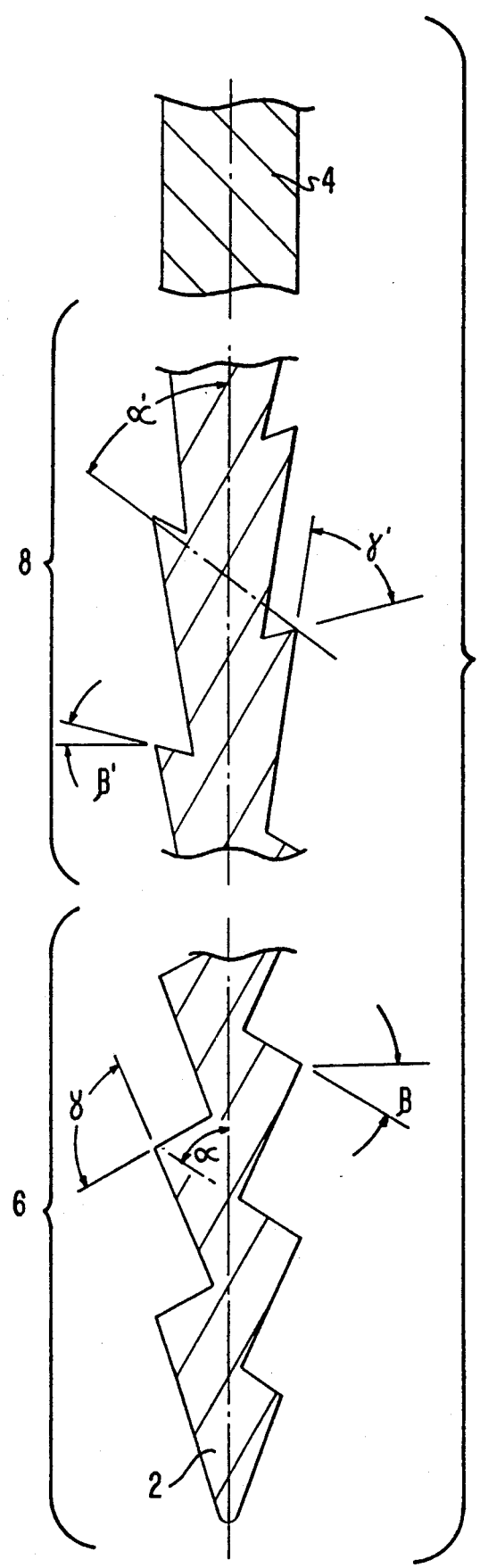

ENDODONTIC FILES

BACKGROUND OF THE INVENTION

The present invention relates to endodontic files, which are employed in the preparation of tooth canals during endodontic procedures.

Endodontic procedures, which are intended to treat conditions affecting the root canals and roots of teeth, include the removal of diseased and non-vital soft tissue from the canals of a tooth, cleaning and shaping the canals, and finally filling the canals as completely as possible with a suitable filling material. The tooth canals must be shaped and enlarged in order, firstly, to ensure that all root material has been removed and, secondly, to assure that filling material can be introduced into each canal up to the tooth apex.

In such procedures, the, or each, canal of a tooth must first be exposed, or opened, by removing material, including pulp, from the tooth crown. Then a succession of files is employed in each canal in order to perform the required cleaning and shaping operations.

In endodontics, a tooth canal is generally conceptualized as being divided into thirds, these being an upper third which is closest to the tooth crown, an apical third which is closest to the tooth apex and a middle third which extends between the upper and apical thirds. As a general rule, the canal should be shaped so that the upper and middle thirds taper from the crown to the apical third, thereby providing a passage for introduction of the thinnest files into the apical third.

It is known that the desirable properties of endodontic files include flexibility, efficiency, the ability to properly cut the canal wall even over curved canal portions, and the ability to remove debris from the canal.

In order to satisfy the requirements of flexibility, it is generally considered desirable that a file be capable of following high degrees of curvature. Various file designs are adaptable to varying degrees of curvature and special files are normally employed when a canal which is highly curved is encountered.

The requirement for efficiency exists because of the need to cut the canal walls, which are made essentially of dentin, in a reasonably short period of time.

In order to be able to shape a curved portion of a canal, the cutting efficiency of the file should be higher against the wall which defines the convex side of the curved path than against the wall defining the concave side thereof.

As regards debris removal, it is essential that debris created during shaping of a canal be removed from the tooth prior to filling. This is achieved by giving the file a greater efficiency when being pulled than when being pushed. Thus, the greater efficiency exists when the file is being moved in a direction out of the canal.

The basic approach to increasing flexibility is to reduce the cross section of the file, which will be determined by the starting diameter of the stock employed to form the file and the form in which the file flutes are ground. As the depth of the flutes increases, the cross section of the file decreases and the instrument becomes more flexible. In addition, the sharper the cutting edge of the file the less metal will be present in its cross section. Of course, the cross section of a file cannot be reduced indefinitely since a smaller cross section reduces the ability of the file to withstand axial stresses, and thus the danger of the distal end of the file becoming broken in a tooth canal.

The efficiency of a file essentially relates to the angle of the cutting edge, or the cutting angle. It is generally considered that a file is most efficient with a cutting angle of 0° to 22.5°, the angle being that which exists between the surface which defines the leading edge of the blade and a plane normal to the axis of the file. The leading edge of the blade is that which faces the blade handle since the cutting action is to be effected by pulling motions. Endodontic files may have a negative cutting angle, which will be less efficient, but is employed under certain circumstances.

During the course of preparation of a tooth canal, a number of different types of files may be called upon to perform different functions. Two types of files which are widely used in these procedures are those known as k files and the Hedstrom files.

The k file is characterized by a relatively short pitch, a small cross-sectional area and a cutting angle in the neighborhood of 0°, while a Hedstrom file is characterized by a larger pitch, a larger cross-sectional area and a larger positive cutting angle. Because of the different cutting properties possessed by files of these types, it is generally considered desirable to utilize a k file to enlarge and shape the apical third of a canal and Hedstrom files to perform this function with respect to the upper and middle thirds.

It is also known that the configuration of the tip of an endodontic file can have a decisive effect on the preparation of curved canals. During the cutting of such a canal, if the cutting edge in the vicinity of the tip is relatively aggressive with respect to the convex side of the canal, the tip will be urged toward the center of the canal. However, such a tip can give rise to a condition known as zipping. A tip with a small angle and a rounded end can alleviate this problem.

In a typical endodontic procedure, after a canal has been opened, Hedstrom files will be employed to shape and enlarge the upper and middle thirds, after which recourse is had to k files to prepare the apical third.

SUMMARY OF THE INVENTION

It is a primary object of the present invention to reduce the number of individual operations which must be performed during the preparation of a tooth canal.

Another object of the invention is to increase the safety of files employed for the operations described above.

Certain of the above and other objects of the invention are achieved by the provision of an endodontic file having a handle, a distal end remote from the handle and formed to have a first file portion which is adjacent the distal end and has the physical form of a k file, and a second file portion, which is located between the first portion and the handle and has the physical form of a Hedstrom file.

As regards the behavior of the tip, it is known that its tendency to create a ledge can be reduced by giving the tip a rounded axial extremity. However, the cutting edge adjacent the tip will cause the tip to be more aggressive.

BRIEF DESCRIPTION OF THE DRAWING

The Figure is an elevational cross-sectional view of one preferred embodiment of the blade portion of a file according to the present invention.

DESCRIPTION OF THE PREFERRED EMBODIMENTS

One preferred embodiment of a file according to the present invention is illustrated in cross section in the sole Figure. The sole Figure shows, in particular, three sections of the file, including a distal end section which terminates in a tip 2 and has the form of a k file, a second portion which is a continuation of the first portion and which has the form of a Hedstrom file, and a proximal portion at which there is provided a handle 4.

A file according to the present invention is preferably cut from a metal shank of circular cross section, having a diameter of between 60 and 1400 microns. As is typical for dental files, the shank may be made of a metal such as stainless steel or a nickel-titanium alloy, which produces greater flexibility. Such a shank is then cut in a known manner, by a suitable cutting machine, to have the configuration shown in the Figure. Thus, according to preferred embodiments of the invention, the desired file structure is created by machining and not by twisting.

At the distal end of the file, there is provided the tip 2 which preferably encloses a conical angle of the order of 40° and has a blunt, or rounded, end. The file is formed to have a helical blade which is oriented in the distal region of the file to have a negative cutting angle, $\beta$. In this portion of the file, which constitutes a k file, the blade is formed to have a helical angle $\alpha$ and a blade angle, $\delta$.

Similarly, the portion 8 of the file which is spaced from the distal end has the form of a Hedstrom file, with a helical angle $\alpha'$, a cutting angle $\beta'$, and a blade angle $\delta'$.

The various angles mentioned above and the axial length of each portion 6, 8 may have values in the ranges set forth on the following table.

TABLE

|  | k file portion 6 | Hedstrom file portion 8 |
|---|---|---|
| Helical angle, $\alpha, \alpha'$ | 40°–70° | 40°–70° |
| Cutting angle, $\beta, \beta'$ | −45°—−20° | 0–45° |
| Blade angle, $\delta, \delta'$ | 40°–70° | 20°–50° |
| Axial length | 2–4 mm | 12–18 mm |

Preferred values for the parameters listed on the above table are as follows: $\alpha = -60°$; $\alpha' = 40°$; $\beta = 25°$ to $-35°$ and most preferably $-30°$; $\beta = 10°-20°$; axial length of portion $6 = 4$ mm; and axial length of portion $8 = 12$ mm.

The negative cutting angle, $\beta$, selected for portion 6 creates a large blade angle between the first turn of the cutting blade and tip 2, thereby reducing the lateral aggressiveness of the tip portion of the file.

Preferably, the conical angle of tip 2 and the cutting angle presented by the cutting edge adjacent tip 2 are selected in order to reduce the lateral aggressiveness of the tip portion of the file. Specifically, when tip 2 encompasses a conical angle of 20°–50°, and the cutting edge is formed to have a negative cutting angle adjacent tip 2, the cutting edge in this region will have a relatively large blade angle and thus will have a reduced aggressiveness.

In the use of a file according to the present invention, portion 6 would be effective in the apical third of a tooth canal, while portion 8 would be effective in the upper and middle thirds thereof. The negative cutting angle $\beta$ and larger blade angle $\gamma$ in portion 6 produces a finer cutting action, while the positive cutting angle $\beta'$ and the smaller blade angle $\gamma'$ in portion 8 produces a more aggressive, or coarser, cutting action. In addition, the combination of the larger helical angle, $\alpha'$ and the taper between turns of the cutting edge in portion 8 gives that portion a greater flexibility.

In general, the flexibility is a function of the cross-sectional area of the file, which means that, for a given value of $\beta$ or $\beta'$, the flexibility can be increased by increasing the value of $\gamma$ or $\gamma'$, respectively.

When a file according to the present invention is constructed so that the helical angle varies progressively in portion 8, as described above, the effectiveness of the file along the entire length of the canal can be enhanced.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

I claim:

1. An endodontic file comprising a handle and an elongate cutting portion, said cutting portion having a distal end remote from the handle, a first file portion which is adjacent the distal end and has the physical form of a k file, and a second file portion which is located between the first portion and the handle and has the physical form of a Hedstrom File.

2. A file as defined in claim 1 wherein said cutting portion is formed from a shank having a circular cross section.

3. A file as defined in claim 2 wherein said cutting portion has a helical cutting edge which extends along said cutting portion with a helical angle, and wherein the helical angle has a first value in said first file portion and a second value, which is different from said first value, in said second file portion.

4. A file as defined in claim 3 wherein the value of the helical angle varies progressively in said second file portion.

5. A file as defined in claim 4 wherein said cutting edge is formed to have a cutting angle which has a negative value in said first file portion and a value of between zero and a positive value in said second file portion.

6. A file as defined in claim 5 wherein the cutting angle has a value of between −25° and −35° in said first file portion.

7. A file as defined in claim 6 wherein the cutting angle has a value of −30° in said first file portion.

8. A file as defined in claim 7 wherein the cutting angle has a value of 10°–20° in said second file portion.

9. A file as defined in claim 8 wherein said cutting portion is further provided, at the extremity of said distal end, with a tip having a blunt end.

10. A file as defined in claim 9 wherein said cutting portion is formed from a circular shank having an initial diameter of 60–1400 micron.

11. A file as defined in claim 10 wherein said shank is made of a material selected from stainless steel and nickel-titanium alloys.

* * * * *